(12) United States Patent  
Echigo (10) Patent No.: US 10,795,142 B2  
(45) Date of Patent: Oct. 6, 2020

(54) CELL-IMAGE ACQUISITION DEVICE

(71) Applicant: OLYMPUS CORPORATION, Tokyo (JP)

(72) Inventor: Hitoshi Echigo, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/667,971

(22) Filed: Oct. 30, 2019

(65) Prior Publication Data

US 2020/0064610 A1    Feb. 27, 2020

Related U.S. Application Data

(63) Continuation of application No. PCT/JP2017/018090, filed on May 12, 2017.

(51) Int. Cl.
*G02B 21/26*    (2006.01)
*G02B 21/36*    (2006.01)
(Continued)

(52) U.S. Cl.
CPC .......... *G02B 21/082* (2013.01); *G02B 21/26* (2013.01); *G02B 21/361* (2013.01); *G02B 21/362* (2013.01); *H04N 5/2256* (2013.01)

(58) Field of Classification Search
CPC .............................. G02B 21/082; G02B 21/26
See application file for complete search history.

(56) References Cited

U.S. PATENT DOCUMENTS 5,260,871 A * 11/1993 Goldberg ............... G16H 50/20  
600/320  
6,956,961 B2 * 10/2005 Cong ..................... G01N 15/14  
382/133

(Continued)

FOREIGN PATENT DOCUMENTS

JP    2010-216920 A    9/2010  
JP    2011-008188 A    1/2011

(Continued)

OTHER PUBLICATIONS

International Search Report dated Aug. 1, 2017 issued in PCT/JP2017/018090.

*Primary Examiner* — Irfan Habib  
(74) *Attorney, Agent, or Firm* — Scully, Scott, Murphy & Presser, P.C.

(57) ABSTRACT

A cell-image acquisition device includes: a stage supporting a vessel containing a cell and a culture fluid; a light source emitting illumination light; a focusing lens disposed below the stage and focusing, when the illumination light is made to enter from above a liquid surface of the culture fluid, light transmitted through the vessel; an aperture disposed so as to block part of the focused light; an image acquisition element acquiring an image of light passing through the aperture and having pixels arrayed in a straight line; a movement mechanism including guide rails and a motor and moving the light source, the focusing lens, the aperture, and the image acquisition element, relative to the stage, in a horizontal direction perpendicular to an array direction of the pixels; and a controller adjusting an incident angle of the illumination light on the liquid surface, about an axis parallel to the array direction.

14 Claims, 8 Drawing Sheets

(51) Int. Cl.
*G02B 21/08* (2006.01)
*H04N 5/225* (2006.01)

(56) References Cited

U.S. PATENT DOCUMENTS

| | | | | |
|---|---|---|---|---|
| 6,962,789 B2 * | 11/2005 | Bacus | ............... | G01N 33/5011 |
| | | | | 422/52 |
| 6,996,549 B2 * | 2/2006 | Zhang | ................... | G06K 9/623 |
| | | | | 706/16 |
| 7,155,050 B1 * | 12/2006 | Sloge | ................ | G06K 9/00127 |
| | | | | 382/133 |
| 7,760,927 B2 * | 7/2010 | Gholap | ............. | G06K 9/00127 |
| | | | | 382/133 |
| 7,801,361 B2 * | 9/2010 | Binnig | ............... | G06K 9/00127 |
| | | | | 382/227 |
| 7,936,913 B2 * | 5/2011 | Nordell | ................ | G06F 19/321 |
| | | | | 382/134 |
| 8,350,905 B2 * | 1/2013 | Yamada | ............ | G01N 21/6458 |
| | | | | 250/306 |
| 8,642,349 B1 * | 2/2014 | Yeatman | ........... | G01N 33/6851 |
| | | | | 436/86 |
| 8,644,582 B2 * | 2/2014 | Yoshihara | ........ | G06K 9/0014 |
| | | | | 382/133 |
| 9,239,281 B2 * | 1/2016 | Manri | ................. | G01N 15/147 |
| 10,304,188 B1 * | 5/2019 | Kumar | ................ | G06K 9/0014 |
| 2002/0001586 A1 * | 1/2002 | Liau | ................... | A61K 39/0011 |
| | | | | 424/155.1 |
| 2008/0166035 A1 * | 7/2008 | Qian | ..................... | G06T 7/0012 |
| | | | | 382/133 |
| 2008/0279441 A1 * | 11/2008 | Matsuo | ............. | G01N 33/5008 |
| | | | | 382/133 |
| 2009/0252728 A1 * | 10/2009 | Jakobovits | ....... | G01N 33/57484 |
| | | | | 424/135.1 |
| 2009/0317836 A1 * | 12/2009 | Kuhn | .................. | G01N 33/574 |
| | | | | 435/7.23 |
| 2009/0326359 A1 * | 12/2009 | Hendriks | ............ | A61B 5/6852 |
| | | | | 600/407 |
| 2010/0232674 A1 * | 9/2010 | Amakawa | .......... | G06K 9/00134 |
| | | | | 382/133 |
| 2011/0019897 A1 * | 1/2011 | Takagi | ..................... | G06T 7/12 |
| | | | | 382/133 |
| 2011/0019898 A1 * | 1/2011 | Takagi | ............... | G06K 9/00147 |
| | | | | 382/133 |
| 2012/0052063 A1 * | 3/2012 | Bhargava | ................ | A61P 35/00 |
| | | | | 424/133.1 |
| 2012/0082362 A1 * | 4/2012 | Diem | ..................... | G01N 21/31 |
| | | | | 382/133 |
| 2012/0177280 A1 * | 7/2012 | Zhukov | ................ | G01N 33/574 |
| | | | | 382/133 |
| 2013/0071876 A1 * | 3/2013 | Hao | ....................... | G01N 23/04 |
| | | | | 435/40.52 |
| 2013/0094750 A1 * | 4/2013 | Tasdizen | .............. | G06K 9/0014 |
| | | | | 382/134 |
| 2013/0182936 A1 * | 7/2013 | Yoshihara | ................. | G06T 7/11 |
| | | | | 382/133 |
| 2014/0080731 A1 * | 3/2014 | Davicioni | ........... | C12Q 1/6886 |
| | | | | 506/9 |
| 2014/0139625 A1 * | 5/2014 | Mathuis | ................. | G06F 16/51 |
| | | | | 348/40 |
| 2017/0075097 A1 * | 3/2017 | Dowaki | ................ | G02B 21/14 |
| 2018/0201892 A1 * | 7/2018 | Gomi | ................... | C12M 1/3453 |
| 2018/0210285 A1 * | 7/2018 | Echigo | ................ | G02F 1/13306 |
| 2018/0259685 A1 * | 9/2018 | Echigo | ................ | H04N 5/2254 |
| 2019/0362491 A1 * | 11/2019 | Rees | ..................... | G06K 9/6274 |

FOREIGN PATENT DOCUMENTS

| | | |
|---|---|---|
| JP | 2012-147739 A | 8/2012 |
| JP | 2015-029461 A | 2/2015 |
| JP | 2015-154728 A | 8/2015 |
| JP | 2015-219280 A | 12/2015 |
| JP | 2016-071117 A | 5/2016 |
| WO | WO 2017/030196 A1 | 2/2017 |
| WO | WO 2017/060954 A1 | 4/2017 |
| WO | WO 2017/104017 A1 | 6/2017 |

* cited by examiner

CELL-IMAGE ACQUISITION DEVICE

CROSS-REFERENCE TO RELATED APPLICATIONS

This is a continuation of International Application PCT/JP2017/018090 which is hereby incorporated by reference herein in its entirety.

TECHNICAL FIELD

The present invention relates to a cell-image acquisition device.

BACKGROUND ART

There is a known cell analysis method for acquiring an image of cells and analyzing the state of the cells from the acquired image (for example, see PTL 1). In the cell analysis method of PTL 1, illumination light is radiated from above a cell culture surface under which cells are cultured, a line-shaped photosensor array for detecting light that has been transmitted through the cells is made to slide, below the culture surface, in one horizontal direction perpendicular to the longitudinal axis of the photosensor array, and an image is acquired.

CITATION LIST

Patent Literature

{PTL 1} Japanese Unexamined Patent Application, Publication No. 2015-154728

SUMMARY OF INVENTION

According to one aspect, the present invention provides a cell-image acquisition device including: a stage that supports a vessel containing a cell together with a culture fluid; a light source that emits illumination light; a focusing lens that is disposed below the stage and that focuses, when the illumination light emitted from the light source is made to enter from above a liquid surface of the culture fluid, light transmitted through the vessel; an aperture that is disposed so as to block part of the light focused by the focusing lens; an image acquisition element that acquires an image of light passing through the aperture and that has a plurality of pixels arrayed in a straight line; a movement mechanism that includes guide rails and a motor and that moves the light source, the focusing lens, the aperture, and the image acquisition element, relative to the stage, in a horizontal direction perpendicular to an array direction of the pixels; and a controller that adjusts an incident angle of the illumination light on the liquid surface of the culture fluid, about an axis parallel to the array direction of the pixels of the image acquisition element.

DESCRIPTION OF EMBODIMENTS

A cell-image acquisition device 1 according to one embodiment of the present invention will be described below with reference to the drawings.

Figure 1:
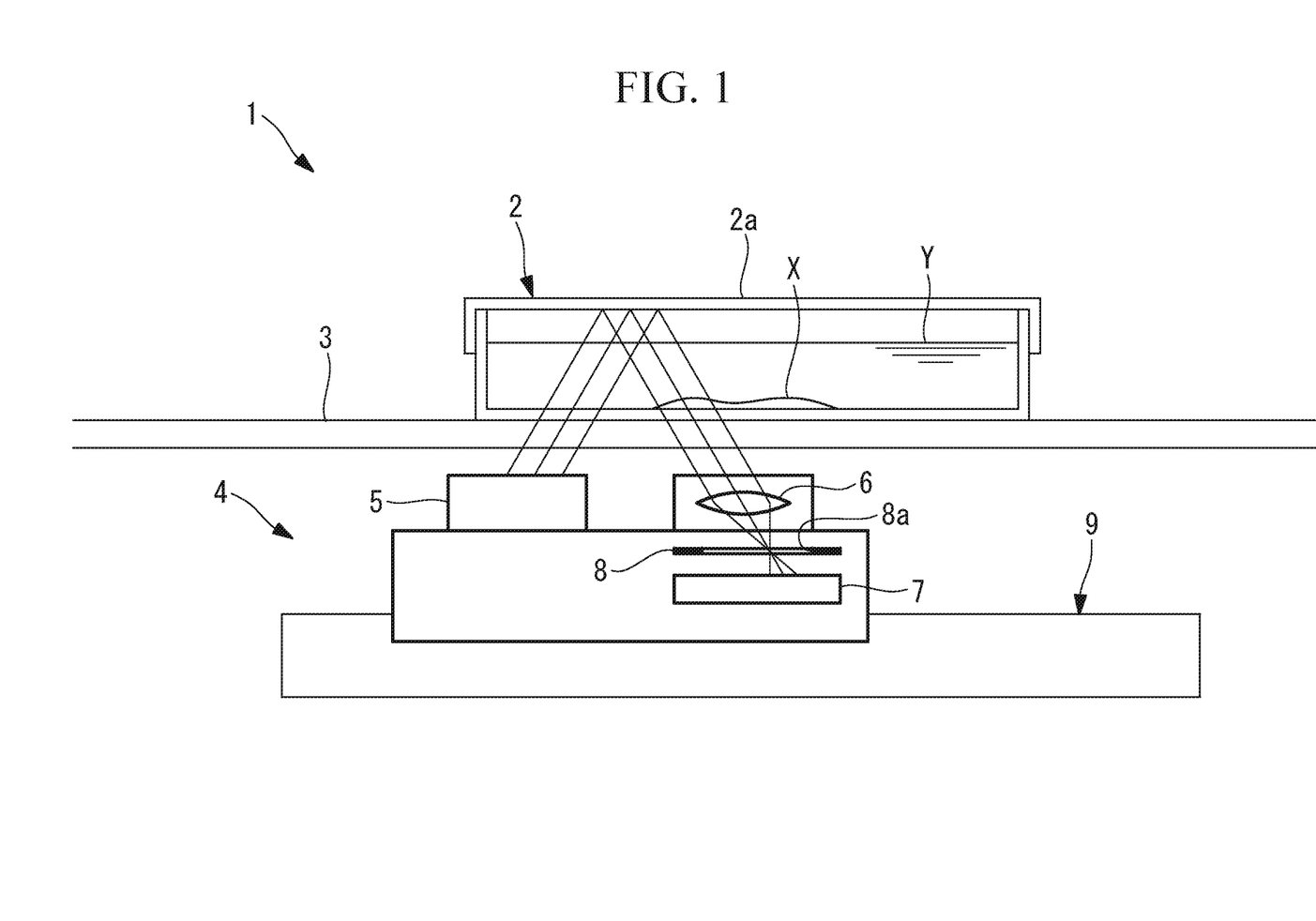
FIG. 1 is a view showing the overall configuration of a cell-image acquisition device according to one embodiment of the present invention.

As shown in FIG. 1, the cell-image acquisition device 1 of this embodiment includes: a stage 3 on which a vessel 2 that contains cells X together with a culture fluid Y is installed and that horizontally supports the vessel; and a scanner 4 that is disposed below the stage 3 and that is provided so as to be movable in the horizontal direction with respect to the stage 3.

The stage 3 has, in at least part thereof, a transparent section that can transmit light.

Figure 2:
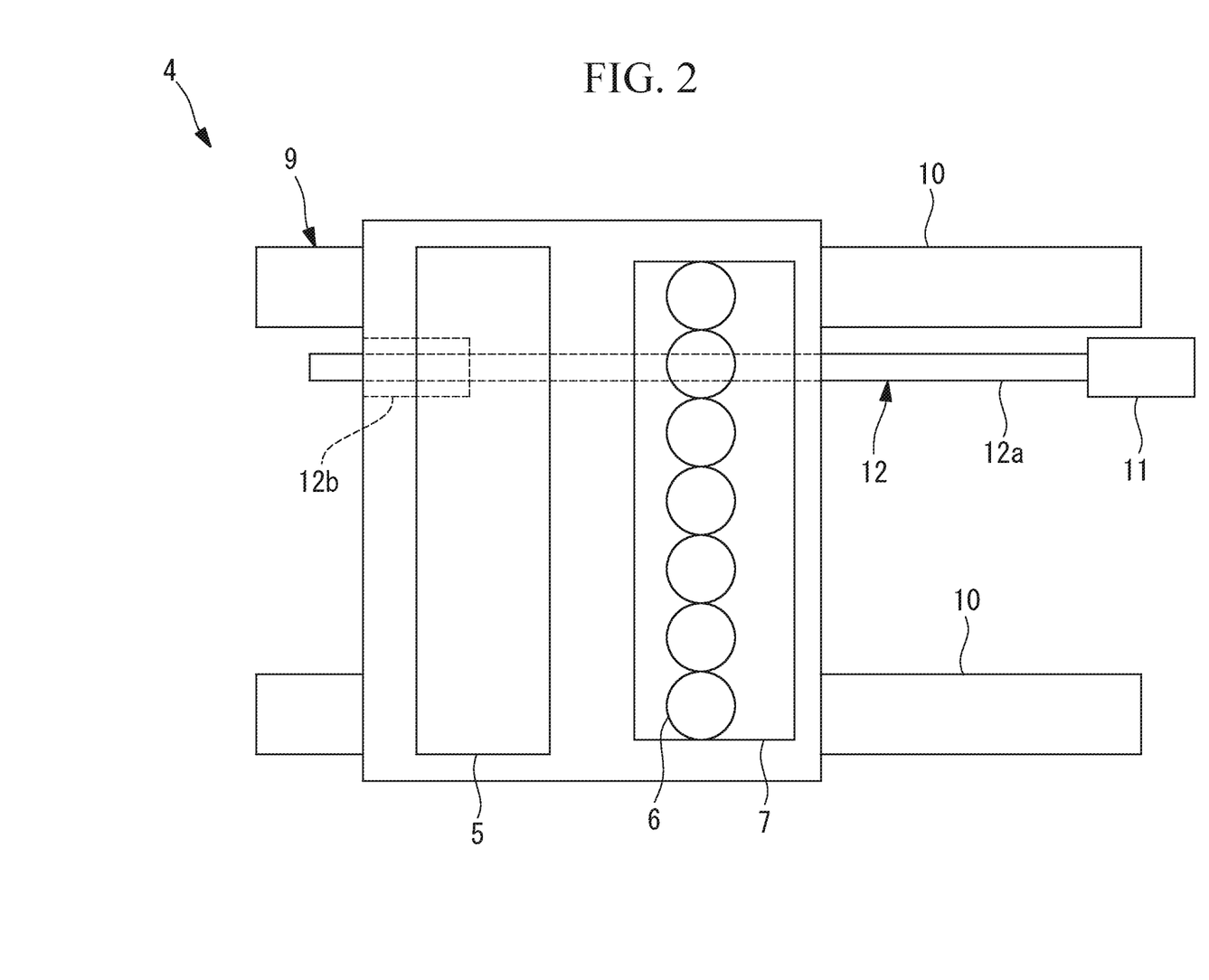
FIG. 2 is a plan view showing the cell-image acquisition device shown in FIG. 1.

The scanner 4 includes: a light source 5 that emits illumination light obliquely upward from below the stage 3; a focusing lens 6 that focuses light entering from obliquely above via the transparent section of the stage 3; an image acquisition element 7 that detects the light focused by the focusing lens 6; an aperture 8 that is disposed between the focusing lens 6 and the image acquisition element 7; and a movement mechanism 9 that moves the light source 5, the focusing lens 6, the aperture 8, and the image acquisition element 7 in one horizontal direction. As shown in FIG. 2, the movement mechanism 9 includes: guide rails 10 that guide the movement in the horizontal direction; a motor 11; and a ball screw 12. In the figure, reference sign 12a denotes a screw shaft, and reference sign 12b denotes a nut.

Furthermore, the scanner 4 includes an illumination-angle adjustment part 13 that moves the light source 5.

As shown in FIG. 2, the image acquisition element 7 is a line sensor that includes a plurality of pixels arrayed in a direction perpendicular to the direction of movement of the movement mechanism 9. The focusing lens 6 is a lens array that includes a plurality of lenses arrayed, in the pixel array direction, corresponding to the respective pixels of the image acquisition element 7.

Figure 3:
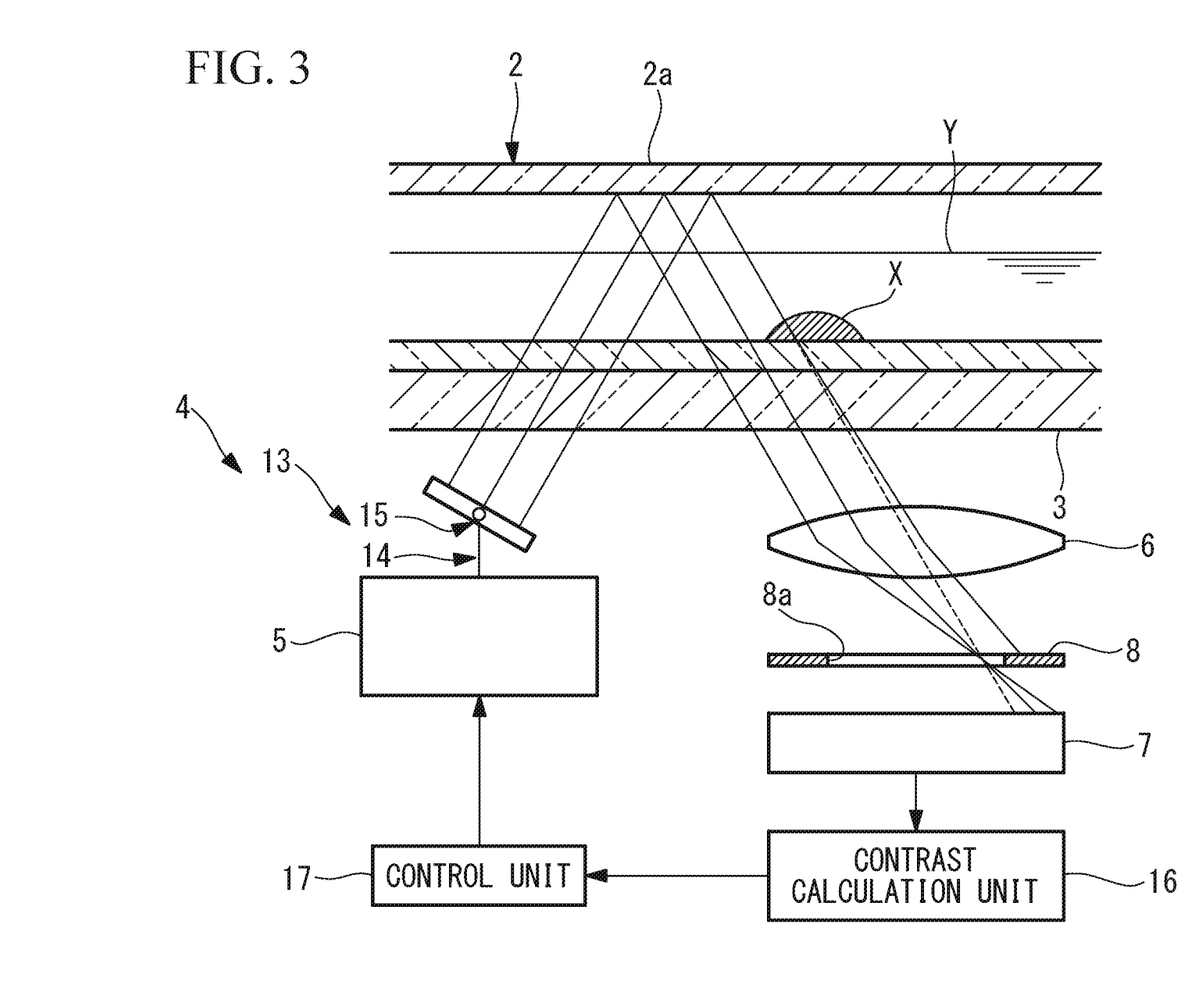
FIG. 3 is a view for explaining acquisition of an image of cells by using the cell-image acquisition device shown in FIG. 1.

As shown in FIG. 2, the light source 5 has an elongated shape extending and disposed in the pixel array direction of the image acquisition element 7 and is disposed below the stage 3 so as to face obliquely upward. As shown in FIG. 3, illumination light emitted from the light source 5 is transmitted, obliquely upward, through the transparent section of the stage 3, a bottom surface of the vessel 2, and the culture fluid Y, is reflected at a lower surface of a top plate 2a of the vessel 2, and is again incident on a liquid surface of the culture fluid Y from obliquely above.

As shown in FIG. 3, the aperture 8 is disposed at such a position that, of the illumination light entering obliquely downward from above the culture fluid Y, the aperture 8 allows light that has been transmitted through the vessel 2 without having passed through the cells X and that has been focused by the focusing lens 6 to pass therethrough and blocks light that has passed through the cells X, thereby being refracted by the cells X, and that has been focused by the focusing lens 6.

For example, in a case in which the illumination light is substantially parallel light, the aperture 8 is disposed in the vicinity of the focal plane of the focusing lens 6, light that has entered the focusing lens 6 as is in the form of substantially parallel light, without having passed through the cells X, is allowed to pass through a through-hole 8*a* provided at the center of the aperture 8, and light that has been refracted by the cells X deviates from the through-hole 8*a*, thus being blocked.

Because illumination light usually has a certain divergence angle, the illumination light is not focused at one point even in the focal plane of the focusing lens 6 but is focused with some degree of spreading. It is desired that the aperture 8 be disposed at such a position as to block about half of the light with some degree of spreading. Accordingly, half of the light that does not pass through the cells X (background light) is blocked, thus reducing the brightness thereof, and light that passes through the cells X enters the focusing lens 6 at an angle different from the background light, thus becoming brighter or darker than the background light, depending on the angle.

Figure 4:
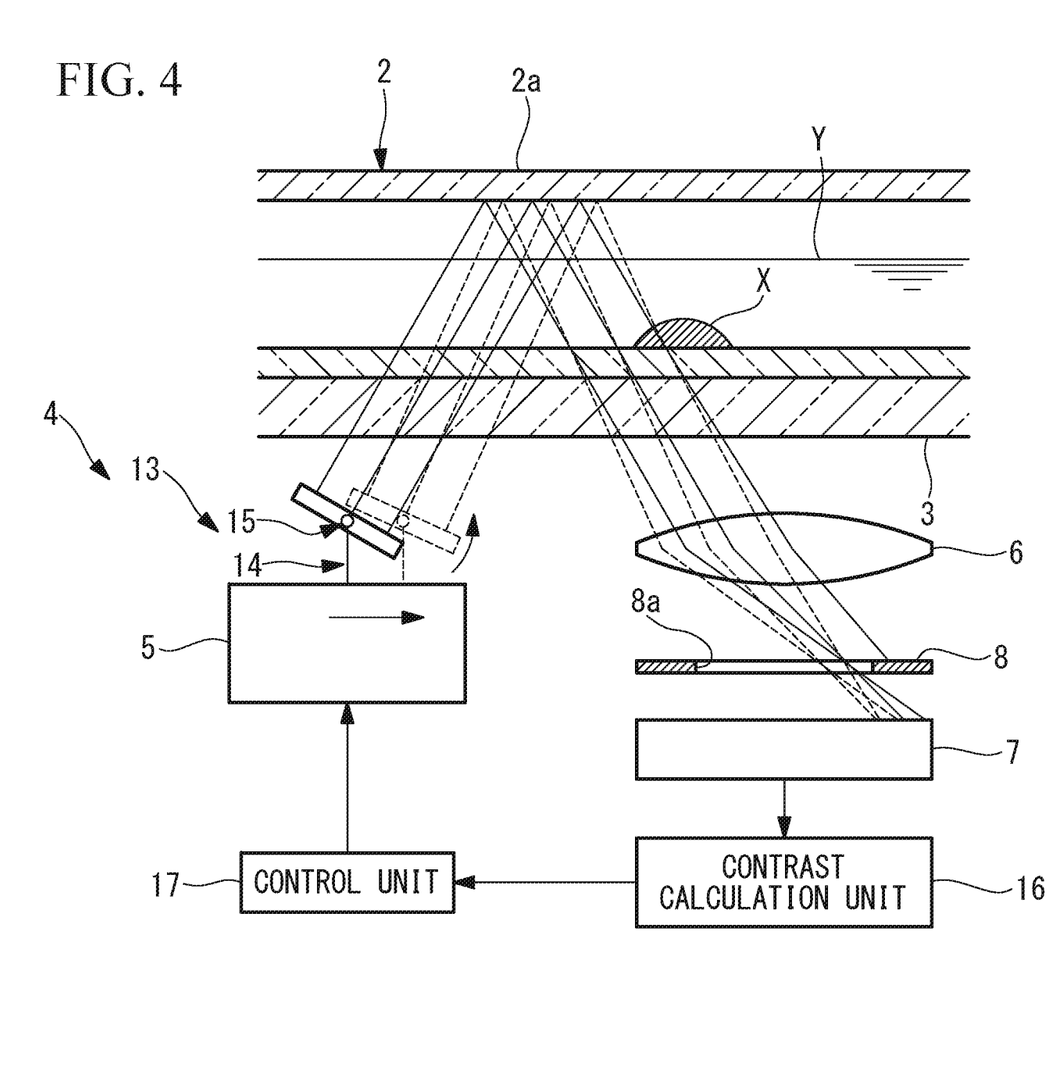
FIG. 4 is a view for explaining an illumination-angle adjustment part of the cell-image acquisition device shown in FIG. 1.

In the example shown in FIGS. 3 and 4, the illumination-angle adjustment part 13 includes: a translation mechanism 14 that translates the light source 5 in a direction along the direction of movement of the movement mechanism 9; and a pivot mechanism 15 that makes the light source 5 pivot about an axis perpendicular to the direction of movement of the movement mechanism 9. Accordingly, when the illumination-angle adjustment part 13 is actuated, the illumination angle of illumination light is adjusted by a combination of the translation of the light source 5 performed by the translation mechanism 14 and the pivoting of the light source 5 performed by the pivot mechanism 15.

More specifically, as shown in FIGS. 3 and 4, the illumination-angle adjustment part 13 includes: a contrast calculation unit 16 that calculates a contrast value from the difference between the maximum value and the minimum value of pixel values output from the plurality of pixels of the image acquisition element 7; and a control unit 17 that controls the translation mechanism 14 and the pivot mechanism 15 such that the contrast value calculated by the contrast calculation unit 16 becomes the maximum. The control unit 17 and the contrast calculation unit 16 are realized by a processor.

The operation of the thus-configured cell-image acquisition device 1 of this embodiment will be described below.

In order to acquire an image of the cells X by using the cell-image acquisition device 1 of this embodiment, first, the light source 5 is disposed at a position and an angle such that illumination light that is emitted upward from the light source 5 is transmitted through the transparent section of the stage 3, the bottom surface of the vessel 2, and the culture fluid Y, is reflected at the top plate 2*a* of the vessel 2, the top plate 2*a* being disposed above the culture fluid Y, is incident on the liquid surface of the culture fluid Y from obliquely above, is transmitted through the culture fluid Y, the bottom surface of the vessel 2, and the transparent section of the stage 3, and is focused by the focusing lens 6, and about half of the light flux of the focused light is blocked by the aperture 8. Then, the movement mechanism 9 is actuated, thereby acquiring an image by means of the image acquisition element 7.

As described above, due to the refractive-index difference between the cells X and the culture fluid Y, light that passes through the cells X and background light that does not pass through the cells X enter the focusing lens 6 at different angles and are focused at different positions in the focal plane. By using this mechanism, it is possible to acquire an image in which the image of the cells X is made brighter or darker to stand out from the background light.

Figure 5:
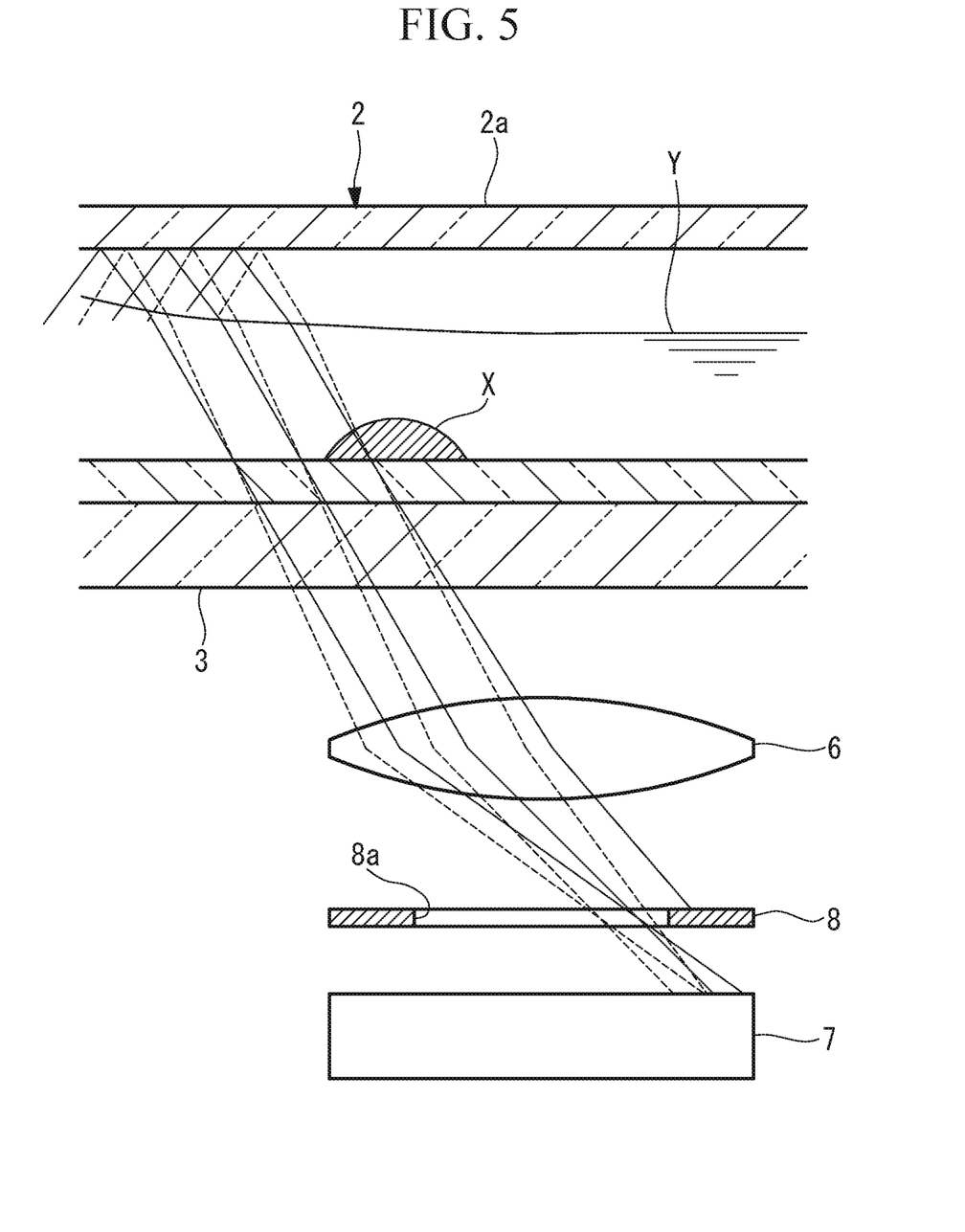
FIG. 5 is a view for explaining a case in which the liquid surface of a culture fluid in a vessel that contains the cells is curved, in the cell-image acquisition device shown in FIG. 1.

In this case, as shown in FIG. 5, when a meniscus occurs on the liquid surface of the culture fluid Y due to surface tension or the like, the top plate 2*a* of the vessel 2 is inclined, or the height of the liquid surface of the culture fluid Y fluctuates, if image acquisition is performed while maintaining the incident angle of illumination light, as indicated by chain lines in FIG. 5, the angle of the light entering the focusing lens 6 changes, thus allowing light that has passed through the cells X and that would have been vignetted by the aperture 8 to pass through the through-hole 8*a*, and reducing the contrast of the cells X. Alternatively, as a result of changing the angle of light entering the focusing lens 6, if the background light is vignetted by the aperture 8, the background becomes dark, thus reducing the visibility.

According to this embodiment, in such cases, the illumination-angle adjustment part 13 is actuated to adjust the incident position and the incident angle of illumination light on the liquid surface of the culture fluid Y, as indicated by solid lines in the FIG. 5, thereby making it possible to acquire a high-contrast image in which the cells X are made to stand out from the background while maintaining a condition in which part of the light that has been focused by the focusing lens 6 is vignetted by the aperture, even when a meniscus occurs on the liquid surface of the culture fluid Y due to surface tension or the like, the top plate 2*a* of the vessel 2 is inclined, or the height of the liquid surface of the culture fluid Y fluctuates.

Note that, in this embodiment, the light source 5 is disposed below the stage 3, and illumination light is emitted obliquely upward and is reflected at the top plate 2*a* of the vessel 2. Accordingly, the height of the cell-image acquisition device 1 can be reduced. Instead of this, in a case in which there is a space above the stage 3, it is also possible to dispose the light source 5 at such a position as to sandwich the vessel 2 between the light source 5 and the stage 3 and to make illumination light enter the vessel 2 from obliquely above.

Figure 6:
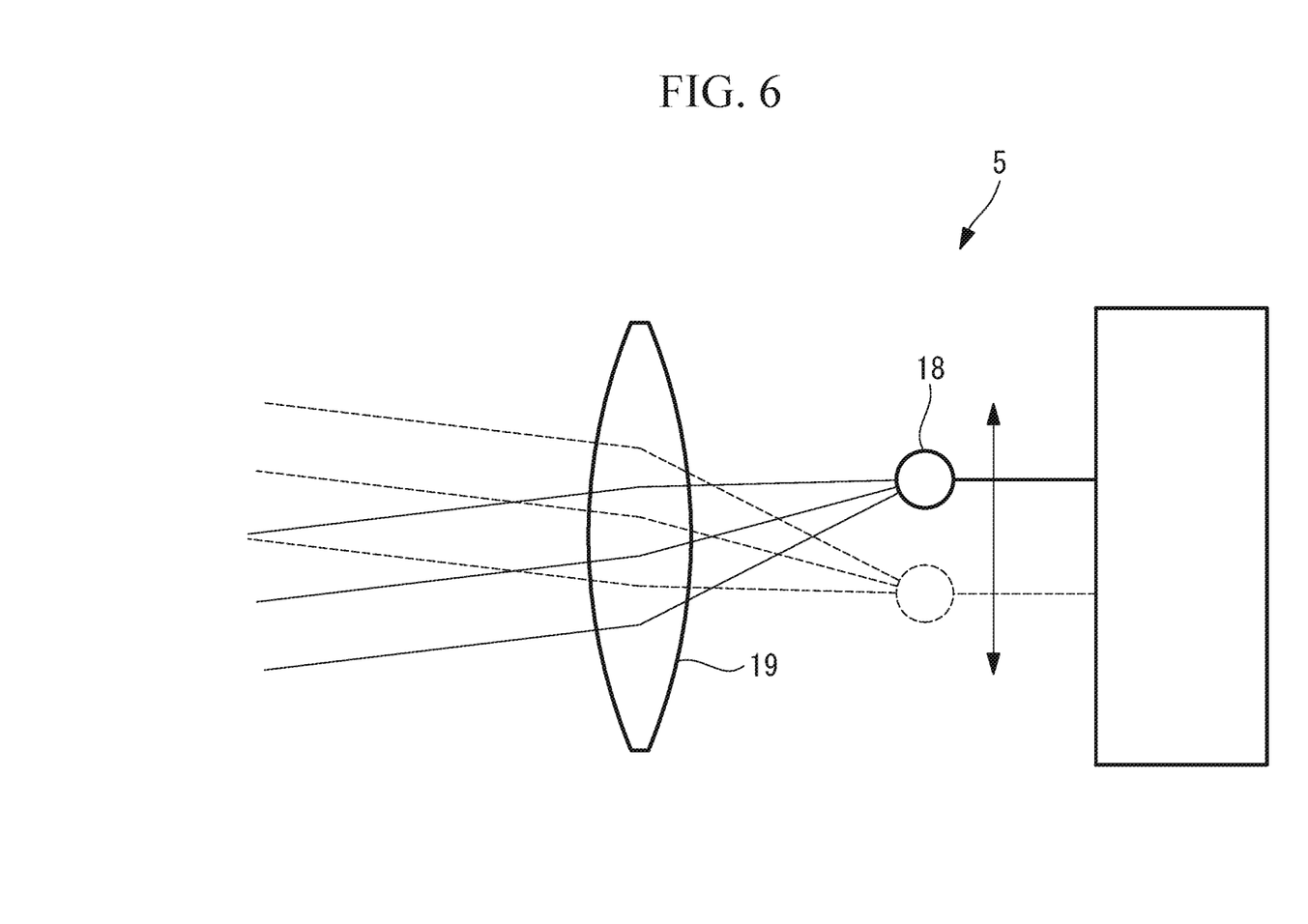
FIG. 6 is a view showing a first modification of the illumination-angle adjustment part shown in FIG. 4.

Furthermore, as shown in FIG. 6, it is also possible to adopt a light source 5 that includes a point light source 18, and a collecting lens (illumination collecting lens) 19, preferably, a collimating lens, that collects light from the point light source 18, and to move the point light source 18 in the horizontal direction relative to the collecting lens 19, thereby changing the angle of illumination light emitted from the collecting lens 19. With the collecting lens 19, it is possible to suppress the divergence angle of the illumination light and to adjust the angle of the illumination light.

Figure 7:
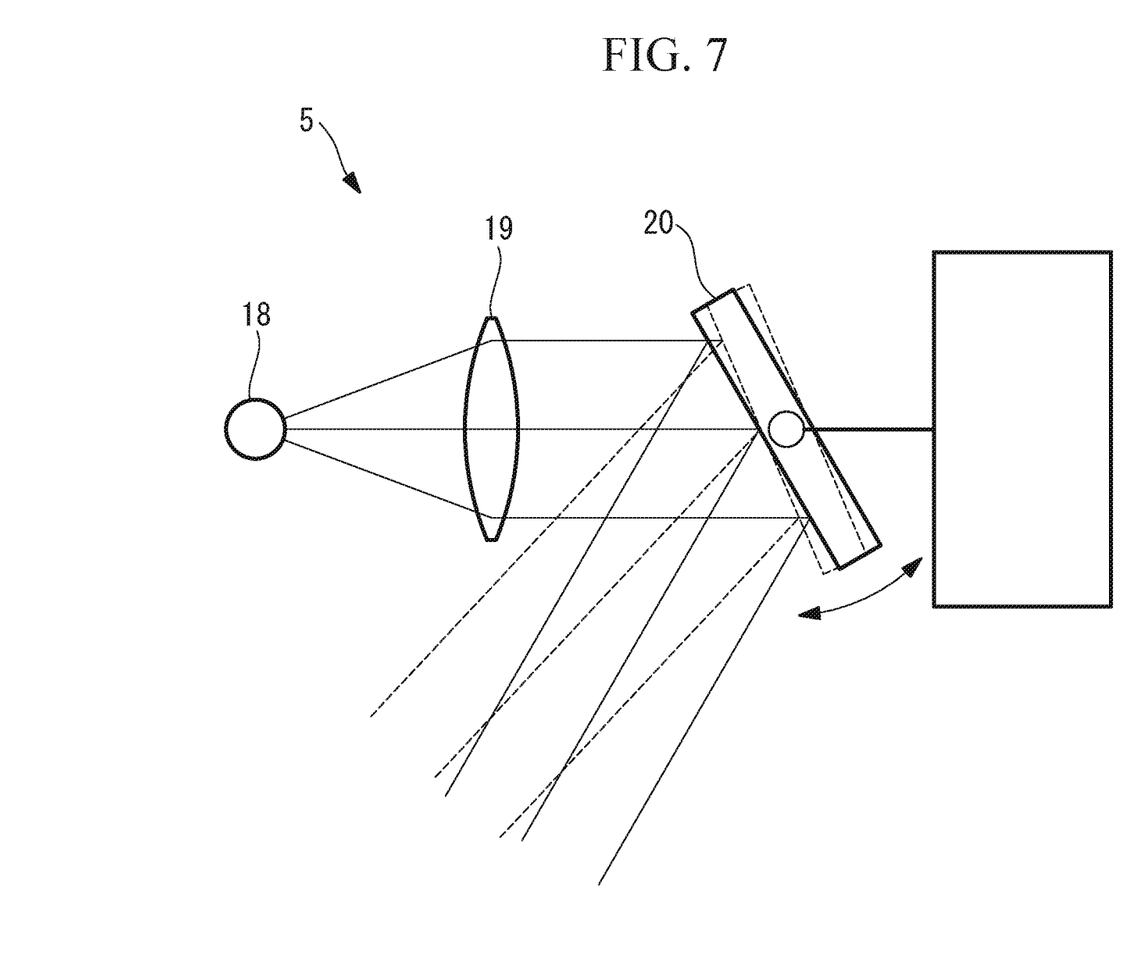
FIG. 7 is a view showing a second modification of the illumination-angle adjustment part shown in FIG. 4.

Furthermore, as shown in FIG. 7, it is also possible to adopt a light source 5 that includes a point light source 18 and a mirror (deflection member) 20 that deflects light from the point light source 18 and to make the deflection member 20 pivot, thereby changing the angle of illumination light.

Figure 8:
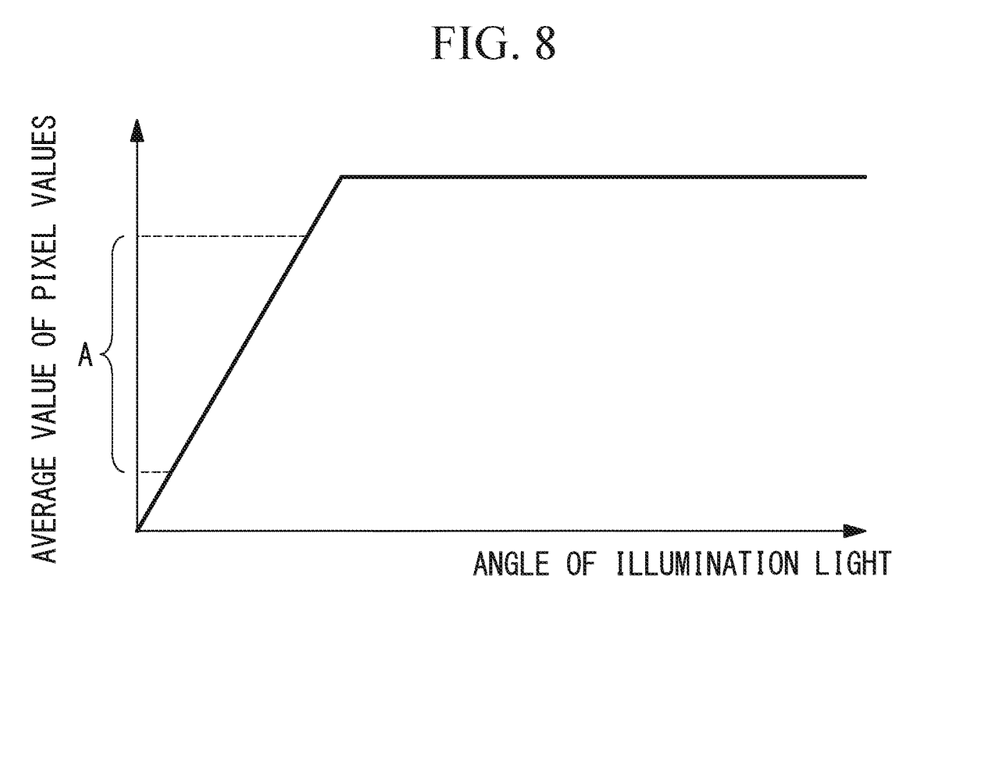
FIG. 8 is a view for explaining a third modification of the illumination-angle adjustment part shown in FIG. 4.

Furthermore, in this embodiment, although the contrast calculation unit 16, which calculates a contrast value from the difference between the maximum value and the minimum value of pixel values obtained from the plurality of pixels of the image acquisition element 7, is adopted, instead of this, it is also possible to adopt an average-value calculation unit that calculates the average value of the pixel values obtained from the plurality of pixels of the image acquisition element 7 and to actuate the illumination-angle adjustment part 13 so as to dispose the average value in a range A shown in FIG. 8.

Figure 9:
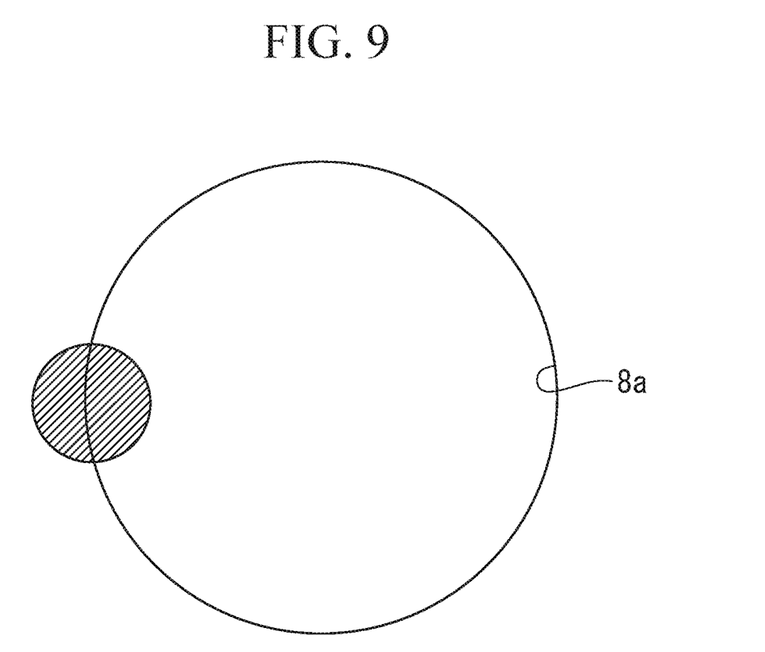
FIG. 9 is a plan view showing the position of a luminous flux of illumination light adjusted with respect to an aperture, in the modification shown in FIG. 8.

Specifically, the range A shown in FIG. 8 is a range in which the average value changes when the incident angle of illumination light is changed, and, as shown in FIG. 9, shows a state in which a luminous flux (indicated by hatching in the figure) focused by the focusing lens 6 is partially vignetted by the aperture 8. Accordingly, it is possible to acquire a high-contrast image in which the cells X are made to stand out from the background. Furthermore, this method has an advantage in that adjustment can be performed even in a state in which cells X are not present, compared with the case in which adjustment is performed such that the contrast value becomes the maximum.

Furthermore, in this embodiment, although the incident angle of illumination light on the culture fluid Y is adjusted in real time, instead of this, it is also possible to obtain, prior to observation, optimum angles by changing the incident angle at a plurality of positions in the direction of movement of the movement mechanism 9 and to determine in advance, for each position therebetween, an incident angle by interpolating the incident angles obtained at the adjacent positions.

The above-described embodiment also leads to the following invention.

According to one aspect, the present invention provides a cell-image acquisition device including: a stage that supports a vessel containing a cell together with a culture fluid; a light source that emits illumination light; a focusing lens that is disposed below the stage and that focuses, when the illumination light emitted from the light source is made to enter from above a liquid surface of the culture fluid, light transmitted through the vessel; an aperture that is disposed so as to block part of the light focused by the focusing lens; an image acquisition element that acquires an image of light passing through the aperture and that has a plurality of pixels arrayed in a straight line; a movement mechanism that moves the light source, the focusing lens, the aperture, and the image acquisition element, relative to the stage, in a horizontal direction perpendicular to an array direction of the pixels; and an illumination-angle adjustment part that adjusts an incident angle of the illumination light on the liquid surface of the culture fluid, about an axis parallel to the array direction of the pixels of the image acquisition element.

According to this aspect, when the vessel, which contains the cell together with the culture fluid, is supported on the stage, and illumination light is emitted from the light source, the illumination light enters the culture fluid from above the liquid surface of the culture fluid. Light that has been transmitted through the vessel is focused by the focusing lens, and an image of light that has passed through the aperture is acquired by the image acquisition element. Because the image acquisition element has the plurality of pixels, which are arrayed in a straight line, when the image acquisition element is horizontally moved relative to the stage in a direction perpendicular to the array direction of the pixels, through actuation of the movement mechanism, it is possible to acquire a two-dimensional image of the bottom surface of the vessel.

In this case, because the refractive index of the culture fluid and the refractive index of the cell in the culture fluid are different from each other, the aperture is disposed such that a condition for allowing light that does not pass through the cell to pass through the aperture and for blocking light that passes through the cell is established by using refraction occurring when light passes through the cell; thus, it is possible to acquire an image in which the cell is made to stand out from the other portions. In this case, even though the aperture is set, as described above, at a position where illumination light passes through a horizontal liquid surface, if illumination light passes through a section of the liquid surface of the culture fluid that is curved due to surface tension or the like, the above-described condition is not established because the illumination light is further refracted at the liquid surface.

According to this aspect, also in such a case, through actuation of the illumination-angle adjustment part, the incident angle of illumination light on the liquid surface of the culture fluid is adjusted about an axis parallel to the array direction of the pixels of the image acquisition element, thereby making it possible to perform adjustment so as to satisfy the above-described condition, i.e., so as to radiate illumination light onto the cell via a desired path, and to acquire a high-contrast image in which the cell is made to stand out.

In the above-described aspect, the illumination-angle adjustment part may adjust the incident angle according to a relative-movement position determined by the movement mechanism.

By doing so, when the movement mechanism moves the light source, the focusing lens, the aperture, and the image acquisition element, relative to the stage, illumination light is made to pass through a different position on the liquid surface of the culture fluid; thus, the illumination-angle adjustment part adjusts the incident angle of the illumination light on the liquid surface, according to the relative movement position, thereby making it possible to acquire a high-contrast image in which the above-described condition is satisfied at every relative movement position.

Furthermore, in the above-described aspect, the illumination-angle adjustment part may change an angle of the light source.

By doing so, the incident angle of illumination light on the liquid surface of the culture fluid can be easily changed by changing the angle of the light source itself.

Furthermore, the above-described aspect may further include a deflection member that deflects the illumination light emitted from the light source, wherein the illumination-angle adjustment part may change an angle of the deflection member.

By doing so, the incident angle of illumination light on the liquid surface of the culture fluid can be easily changed by fixing the light source and changing the angle of the deflection member.

Furthermore, in the above-described aspect, the light source may include a point light source and an illumination collecting lens that collects illumination light from the point light source; and the illumination-angle adjustment part may move the point light source in a direction intersecting an optical axis of the illumination collecting lens.

By doing so, the point light source is moved with respect to the collecting lens in a direction intersecting the optical axis of the collecting lens, thereby making it possible to change the angle of a luminous flux emitted from the collecting lens and to easily change the incident angle of illumination light on the liquid surface of the culture fluid.

Furthermore, the above-described aspect may further include a contrast calculation unit that calculates a contrast value from pixel values output from the respective pixels of the image acquisition element, wherein the illumination-angle adjustment part may adjust the incident angle such that the contrast value calculated by the contrast calculation unit becomes the maximum.

By doing so, the incident angle is adjusted such that the contrast value becomes the maximum at every position of movement of the light source, the focusing lens, the aperture, and the image acquisition element, relative to the stage, the relative movement being performed by the movement mechanism, thereby making it possible to acquire an image in which the overall contrast is high.

Furthermore, the above-described aspect may further include an average-value calculation unit that calculates an average value of pixel values output from the respective pixels of the image acquisition element, wherein the illumination-angle adjustment part may adjust the incident angle within a range in which the average value calculated by the average-value calculation unit changes through a change in the incident angle.

By doing so, even when the liquid surface in a culture vessel changes, it is possible to maintain a state in which part of a luminous flux that has passed through the vessel is allowed to pass through the aperture, and the remaining part is blocked by the aperture, and to acquire a high-contrast image in which the cell is made to stand out.

REFERENCE SIGNS LIST 1 cell-image acquisition device
2 vessel
3 stage
5 light source
6 focusing lens
7 image acquisition element (image sensor)
8 aperture
9 movement mechanism
13 illumination-angle adjustment part
16 contrast calculation unit
18 point light source
19 collecting lens (illumination collecting lens)
20 mirror (deflection member)
X cell
Y culture fluid

The invention claimed is:
1. A cell-image acquisition device comprising:
a stage that supports a vessel containing a cell together with a culture fluid;
a light source that emits illumination light;
a focusing lens that is disposed below the stage and that focuses, when the illumination light emitted from the light source is made to enter from above a liquid surface of the culture fluid, light transmitted through the vessel;
an aperture that is disposed so as to block part of the light focused by the focusing lens;
an image acquisition element that acquires an image of light passing through the aperture and that has a plurality of pixels arrayed in a straight line;
a movement mechanism that comprises guide rails and a motor and that moves the light source, the focusing lens, the aperture, and the image acquisition element, relative to the stage, in a horizontal direction perpendicular to an array direction of the pixels; and
a controller that adjusts an incident angle of the illumination light on the liquid surface of the culture fluid, about an axis parallel to the array direction of the pixels of the image acquisition element.

2. The cell-image acquisition device according to claim 1, wherein the controller adjusts the incident angle according to a relative-movement position determined by the movement mechanism.

3. The cell-image acquisition device according to claim 1, wherein the controller changes an angle of the light source.

4. The cell-image acquisition device according to claim 1, further comprising a mirror that deflects the illumination light emitted from the light source,
wherein the controller changes an angle of the mirror.

5. The cell-image acquisition device according to claim 1,
wherein the light source comprises a point light source and an illumination collecting lens that collects illumination light from the point light source; and
the controller moves the point light source in a direction intersecting an optical axis of the illumination collecting lens.

6. The cell-image acquisition device according to claim 1,
wherein the controller calculates a contrast value from pixel values output from the respective pixels of the image acquisition element and adjusts the incident angle such that the calculated contrast value becomes the maximum.

7. The cell-image acquisition device according to claim 1,
wherein the controller calculates an average value of pixel values output from the respective pixels of the image acquisition element and adjusts the incident angle within a range in which the calculated average value changes through a change in the incident angle.

8. A cell-image acquisition device comprising:
a stage that supports a vessel containing a cell together with a culture fluid;
a light source that emits illumination light;
a focusing lens that is disposed below the stage and that focuses, when the illumination light emitted from the light source is made to enter from above a liquid surface of the culture fluid, light transmitted through the vessel;
an aperture that is disposed so as to block part of the light focused by the focusing lens;
an image acquisition element that acquires an image of light passing through the aperture;
a movement mechanism that comprises guide rails and a motor and that moves the light source, the focusing lens, the aperture, and the image acquisition element relative to the stage; and
a controller that adjusts an incident angle of the illumination light on the liquid surface of the culture fluid.

9. The cell-image acquisition device according to claim 8, wherein the controller adjusts the incident angle according to a relative-movement position determined by the movement mechanism.

10. The cell-image acquisition device according to claim 8, wherein the controller changes an angle of the light source.

11. The cell-image acquisition device according to claim 8, further comprising a mirror that deflects the illumination light emitted from the light source,
wherein the controller changes an angle of the mirror.

12. The cell-image acquisition device according to claim 8,
wherein the light source comprises a point light source and an illumination collecting lens that collects illumination light from the point light source; and the controller moves the point light source in a direction intersecting an optical axis of the illumination collecting lens.

13. The cell-image acquisition device according to claim 8, wherein the controller calculates a contrast value from pixel values output from the respective pixels of the image acquisition element and adjusts the incident angle such that the calculated contrast value becomes the maximum.

14. The cell-image acquisition device according to claim 8, wherein the controller calculates an average value of pixel values output from the respective pixels of the image acquisition element and adjusts the incident angle within a range in which the calculated average value changes through a change in the incident angle.

* * * * *